United States Patent
Kurahashi

(10) Patent No.: US 6,847,697 B2
(45) Date of Patent: Jan. 25, 2005

(54) MEDICAL IMAGE PROCESSING APPARATUS, MEDICAL IMAGE PROCESSING METHOD, PROGRAM AND A RECORDING MEDIUM THEREOF

(75) Inventor: Akira Kurahashi, Hino (JP)

(73) Assignee: Konica Corporation (JP)

( * ) Notice: Subject to any disclaimer, the term of this patent is extended or adjusted under 35 U.S.C. 154(b) by 221 days.

(21) Appl. No.: 10/319,971

(22) Filed: Dec. 16, 2002

(65) Prior Publication Data

US 2003/0123719 A1 Jul. 3, 2003

(30) Foreign Application Priority Data

Dec. 27, 2001 (JP) .......................... 2001-396695

(51) Int. Cl.[7] .............................................. G01N 23/04
(52) U.S. Cl. ........................ 378/62; 378/98; 382/132
(58) Field of Search ................. 378/4, 8, 62, 98, 378/98.2, 901; 382/132

(56) References Cited

U.S. PATENT DOCUMENTS

2003/0194117 A1 * 10/2003 Okuzawa ................. 382/128
2004/0008900 A1 * 1/2004 Jabri et al. ................ 382/254

FOREIGN PATENT DOCUMENTS

JP 2003190127 A * 7/2003 ............ A61B/6/00

* cited by examiner

*Primary Examiner*—David V Bruce
(74) *Attorney, Agent, or Firm*—Cantor Colburn LLP

(57) ABSTRACT

A medical image processor for reading a medical image obtained through radiographing and for outputting the medical image to plural output devices. The medical image processor includes: a characteristics information storage for storing characteristics information, including sampling characteristics information showing resolution of each of the output devices; a reader for reading the medical image obtained through radiographing; and a sampler for conducting sampling of the medical image read by the reader, in use of sampling characteristics information among characteristics information stored in the characteristics information storage, for each of the output devices so that a sampled image is generated.

20 Claims, 11 Drawing Sheets

FIG. 4

OUTPUT CHARACTERISTIC DATA BASE C

| | DISPLAY TERMINAL 2A | DISPLAY TERMINAL 2B | IMAGER 3 | |
|---|---|---|---|---|
| c1 | SAMPLING CHARACTERISTIC DATA | SAMPLING CHARACTERISTIC DATA | SAMPLING CHARACTERISTIC DATA | c5 |
| c2 | IMAGE PROCESSING CHARACTERISTIC DATA | IMAGE PROCESSING CHARACTERISTIC DATA | IMAGE PROCESSING CHARACTERISTIC DATA | c6 | c4    c3

FIG. 10

| SAMPLING INFORMATION | RADIOGRAPHING REGION | RADIOGRAPHING METHOD | REDUCTION RATE | IMAGE ANALYSIS INFORMATION |
|---|---|---|---|---|
| A | ADULT BREAST FRONT | SIMPLE RADIOGRAPHING APPARATUS | 2.8 mm PITCH | ANALYSIS PARAMETER 1 |
| B | INFANT ABDOMEN FRONT | SIMPLE RADIOGRAPHING APPARATUS | 1.4 mm PITCH | ... |
| ... | ... | ... | ... | ... |
| N | ADULT BREAST SECTION | SCANNER | 5.6 mm PITCH | ANALYSIS PARAMETER N |
| ... | ... | ... | ... | ... |

15a

MEDICAL IMAGE PROCESSING APPARATUS, MEDICAL IMAGE PROCESSING METHOD, PROGRAM AND A RECORDING MEDIUM THEREOF

BACKGROUND OF THE INVENTION

The present invention relates to a medical image processing apparatus for processing a medical image, a medical image processing method, its program and a recording medium on which the program is recorded.

For diagnoses of patients in the field of medical treatment, there have been used medical image radiographing apparatuses such as an X-ray radiographing apparatus employing a radiation such as X-ray, RI (Radio Isotope) apparatus, CR (Computed Radiography) apparatus, CT (Computed Tomography) apparatus, a supersonic radiographing apparatus and MRI (Magnetic Resonance Imaging) apparatus.

Images obtained through radiographing by the medical image radiographing apparatus have been converted from analog data in radiographing into digital data through a certain sampling, then, have been subjected to image processing such as frequency processing to be stored as processed image data, and a monitor which outputs on its screen and an imager wherein a film is exposed to light have been used to output the processed image data.

However, in the conventional medical image radiographing apparatus, images obtained through radiographing have been stored after being subjected to a certain sampling. Therefore, when outputting to an outputting apparatus which is different in terms of characteristics such as a type, an apparatus model and resolution, the stored image data are image-processed after being subjected to resolution conversion so that the image data may match each outputting apparatus, and thereby the image-processed image data are outputted. Thus, convertion of resolution is applied at least two times, and image deterioration was not avoided.

For example, when conducting resolution conversion, thinning processing and interpolation processing have deteriorated images. The "resolution conversion" here may be both of resolution gaining operation and resolution reducing operation.

The first subject of the invention is to prevent deterioration of medical images and to output medical images for each outputting apparatus.

Further, in the medical field in recent years, there has been developed a medical image processing apparatus which conducts various types of image processing on medical images inputted as digital images by various types of medical image radiographing apparatuses such as CT (Computed Tomography) apparatus employing radiation and MRI (Magnetic Resonance Imaging) apparatus and by various types of medical image input apparatus such as a medical image reading apparatus like CR (Computed Radiography), and displays on a monitor such as CRT, or outputs on a film. By observing images visualized to become easy to be seen by the medical image processing apparatus of this kind, a doctor can diagnose exactly.

In the aforementioned medical image processing apparatus, analog image data inputted from a medical image input apparatus are stored as original image data in general, and then, the original image data are subjected to sampling for conducting image analysis to generate reduction digital image data at a prescribed reduction rate. Incidentally, the purpose of generating reduction image data is to shorten the time required for the image analysis, and in the image analysis wherein reduction image data are used, it is possible to establish the reduction rate which is mostly the same as that in the occasion where the original image data are used.

Since the medical images are those obtained by radiographing various regions such as abdomen and breast with various medical image radiographing apparatuses such as CT and MRI, as stated above, an area (hereinafter referred to as a region of interest) to be looked by a doctor for each region or for each radiographing condition such as a radiographing method varies. For example, even in the case of images wherein the same breast is radiographed, a position and a shape of a region of interest vary and its information amount also varies, in the case of the radiographing method of simple radiographing to radiograph from the front side and of tomography to radiograph a tomogram. However, in the course of generation of the conventional reduction image data, the prescribed sampling condition is applied to all images, namely, reduction is made for all images at the prescribed reduction rate, without coping with the circumstances mentioned above. Therefore, its reduction rate does not always give efficient image analysis depending on radiographing conditions such as regions to be radiographed and radiographing methods, and there has sometimes been an occasion to lower accuracy of processing of image analysis or to lower the processing speed.

The second subject of the invention is to provide a medical image processing apparatus wherein sampling conditions corresponding to radiographing conditions are prepared in advance, and efficient image analysis can be conducted.

SUMMARY OF THE INVENTION

For solving the first subject stated above, the invention is a medical image processing apparatus that reads medical images obtained through radiographing and outputs the medical images to a plurality of output apparatuses, and it is characterized to be composed of a characteristics information storage means for storing characteristics information including sampling characteristics information showing resolution of each output apparatus, a reading means that reads the aforementioned medical images obtained through radiographing and a sampling means that conducts sampling for the medical images read by the reading means by the use of sampling characteristics information among characteristics information stored in the characteristics information storage means, for each output apparatus.

The invention is further characterized to have, in the aforementioned medical image processing apparatus, an image processing means that image-processes sampled images by the sampling means.

In the medical image processing apparatus stated above, the invention is characterized in that the characteristics information includes image processing characteristics information showing image processing characteristics of each of the output apparatuses, and the image processing means image-processes sampled images by the sampling means by the use of image processing characteristics information among characteristics information stored in the characteristics information storage means.

The invention is further characterized to have, in the aforementioned medical image processing apparatus, an image storage means that stores sampled images by the sampling means.

The invention is further characterized to have, in the aforementioned medical image processing apparatus, an image storage means that stores image-processed image image-processed by the image processing means.

The invention is represented by the medical image processing apparatus for reading sampled medical images and for outputting the medical images to a plurality of output apparatuses, and it is characterized to have a characteristics information storage means that stores characteristics information including image processing characteristics information showing image processing characteristics of each output apparatus stated above, a reading means that reads the sampled medical images mentioned above, and an image processing means that image-processes, for each output apparatus, the sampled images of the medical images read by the reading means by the use of image processing characteristics information among characteristics information stored in the characteristics information storage means.

In the medical image processing apparatus stated above, the invention is characterized in that the characteristics information mentioned above includes sampling characteristics information showing resolution of each of the output apparatuses, a sampling means that samples the sampled image read by the reading means again for each output apparatus is provided by the use of sampling characteristics information among characteristics information stored in the aforementioned characteristics information storage means, is provided, and the image processing means image-processes, for each output apparatus, the images sampled again in the sampling means by the use of image processing characteristics information among characteristics information stored in the characteristics information storage means mentioned above.

Further, the invention is an medical image processing method for reading medical images obtained through radiographing and for outputting the medical images to a plurality of output apparatuses, and it is characterized that the medical images obtained through radiographing are read, then, sampling characteristics information is read as characteristics information from the characteristics information storage means that stores characteristics information including sampling characteristics information showing resolution of each of the output apparatuses, and images read from the medical images read aresolution converted for each of the output apparatuses by the use of the sampling characteristics information read.

Furthermore, the invention is an medical image processing method for reading medical images sampled and for conducting image processing for outputting the medical images to a plurality of output apparatuses, and it is characterized that the medical images sampled are read, then, image processing characteristics information is read as characteristics information from the characteristics information storage means that stores characteristics information including image processing characteristics information showing image processing characteristics of each of the output apparatuses, and sampled images of the read medical images are image-processed for each output apparatus by the use of the read image processing characteristics information.

Further, the invention is a program used with a computer for realizing a function to read medical images obtained through radiographing, a function for reading sampling characteristics information as characteristics information from the characteristics information storage means that stores characteristics information including sampling characteristics information showing resolution of plural output apparatuses, and a function for sampled images read from medical images read by the use of the sampling characteristics information read.

Further, the invention is a program used with a computer for realizing a function to read-out sampled medical images, a function to read image processing characteristics information as characteristics information from characteristics information storage means that stores characteristics information including image processing characteristics information showing image processing characteristics of each of the output apparatuses, and a function for image-processing the sampled image of medical images read out for each output apparatus by the use of the image processing characteristics information read.

Further, the invention is a recording medium which can be read by a computer and has a program for realizing a function to read medical images obtained through radiographing, a function to read sampling characteristics information as characteristics information from a characteristics information storage means that stores characteristics information including sampling characteristics information showing resolution of plural output apparatuses, and a function to sample images to be read in the read medical images for each output apparatus by the use of the read sampling characteristics information.

Further, the invention is a recording medium which can be read by a computer and has a program for realizing a function to read-out sampled medical images, a function to read image processing characteristics information as characteristics information from a characteristics information storage means that stores characteristics information including image processing characteristics information showing image processing characteristics of each of the output apparatuses and a function to image-process sampled images of the read medical images for each output apparatus by the use of the read image processing characteristics information.

In the invention, medical images obtained through radiographing are read, sampling characteristics information is read as characteristics information from a characteristics information storage means, and images to be read in the read medical images aresolution converted for each output apparatus by the use of the sampling characteristics information.

Therefore, in the invention, it is possible to sample medical images obtained through radiographing by making them to correspond to output apparatuses, and thereby to process medical images to output them, by preventing resolution converting which causes image deterioration.

In the invention, sampled images which have been sampled are subjected to image processing.

Therefore, in the invention, it is possible to image-process the sampled sampled images.

Further, in the invention, it is possible to read sampling characteristics information and image processing characteristics information as characteristics information from a characteristics information storage means, then, to sample images to be read in medical images for each output apparatus by the use of the sampling characteristics information, and to image-process by the use of the aforesaid image processing characteristics information.

Therefore, in the invention, it is possible to sample and image-process medical images obtained through radiographing by making them to correspond to output apparatuses, and thereby to output medical images, by preventing resolution converting which causes image deterioration.

In the invention, sampled images in which images to be read in medical images are stored in the image storage means.

In the invention, therefore, if image processing characteristics information is changed to correspond to the output apparatus, stored sampled image can be image-processed based on the changed image processing characteristics information, because sampled images are stored in an image storage means.

Further, in the invention, image-processed images wherein images to be read in medical images are image-processed are stored in an image storage means.

In the invention, therefore, it is possible to output the stored image-processing images again, because image-processing images are stored in an image storage means.

In the invention, sampled medical images are read out, image processing characteristics information is loaded as characteristic information, and sampled images of the medical images read are image-processed for each output apparatus by the use of the image processing characteristics information.

Therefore, in the invention, sampled images of sampled medical images can be image-processed, corresponding to the output apparatus.

In the invention, sampled medical images are read out, sampling characteristics information and image processing characteristics information are loaded as characteristics information, sampled images of the read out medical images are resolution converted for each output apparatus by the use of the sampling characteristics information and are image-processed by the use of the image processing characteristics information.

Therefore, the sampled images of the sampled medical images can be subjected to resolution converting and image processing, corresponding to the output apparatus.

For solving the second subject stated above, another example of the invention is represented by a medical image processing apparatus that conducts image processing on images inputted by a medical image inputting apparatus, wherein, there are provided an original image data storage means that stores the aforesaid inputted image data as original image data, a sampling condition storage means that stores sampling conditions in accordance with radiographing conditions for the images radiographed for each radiographing condition when the original image data aresolution converted and sampled image data are generated, a radiographing condition acquiring means that acquires radiographing conditions for the image inputted from the medical image input apparatus, a sampled image data generating means that reads out sampling conditions corresponding to the acquired radiographing conditions from the sampling condition storage means, and samples the stored original image data according to the sampling condition to generate sampled image data, and an image analysis means that conducts image analysis on the generated sampled image data.

In the medical image processing apparatus mentioned above, the invention is characterized in that the aforesaid sampled image data generating means samples the original image data and generates reduction image data, the sampling condition stated above is a reduction rate which is used when the sampled image data generating means generates the reduction image data, and the reduction rate is one which makes the processing time to be shortest without lowering the processing accuracy for image analysis by the image analysis means.

The invention is represented by an image processing method that conduct image processing on images inputted by a medical image input apparatus, wherein, there are provided a process to store the aforesaid inputted image data in an original image data storage means as an original image data, a process to storesolution converting conditions corresponding to the radiographing conditions for the image obtained through radiographing in a sampling condition storage means for each radiographing condition, when generating sampled image data by sampling the original image data, a process to acquire radiographing conditions for the inputted image from the medical image input apparatus, a process to read sampling conditions corresponding to the acquired radiographing conditions from the sampling condition storage means and to sample the stored original image data in accordance with the sampling conditions to generate sampled image data, and a process to conduct image analyses on the generated sampled image data.

Further, the invention is characterized to be a program for realizing a function to store the aforesaid inputted image data in an original image data storage means as an original image data, a function to storesolution converting conditions corresponding to the radiographing conditions for the image obtained through radiographing in a sampling condition storage means for each radiographing condition, when generating sampled image data by sampling the original image data, to make an original image data storage means to store the inputted image data as an original image data, a function to acquire radiographing conditions for the inputted image from the medical image input apparatus, a function to read sampling conditions corresponding to the acquired radiographing conditions from the sampling condition storage means and to sample the stored original image data in accordance with the sampling conditions to generate sampled image data, and a function to conduct image analyses on the generated sampled image data, in a computer that controls a medical image processing apparatus conducting image processing on the image inputted by a medical image input apparatus.

Further, the invention is represented by a recording medium housing therein a program which can be executed by a computer that controls a medical image processing apparatus that conducts image processing on the image inputted by a medical image input apparatus, wherein there is housed a program that includes a program code which can be executed by a computer that stores the inputted image data in an original image data storage means as original image data, a program code which can be executed by a computer to storesolution converting conditions corresponding to the radiographing conditions for the image obtained through radiographing in a sampling condition storage means for each radiographing condition, when generating sampled image data by sampling the original image data, to make an original image data storage means to store the inputted image data as an original image data, a program code which can be executed by a computer to acquire radiographing conditions for the inputted image from the medical image input apparatus, a program code which can be executed by a computer to read sampling conditions corresponding to the acquired radiographing conditions from the sampling condition storage means and to sample the stored original image data in accordance with the sampling conditions to generate sampled image data, and a program code which can be executed by a computer to conduct image analyses on the generated sampled image data.

In the invention, the reduction rate which makes the processing time to be shortest without lowering the processing accuracy for image analysis is stored in advance, corresponding to the radiographing conditions of the image, then, the radiographing conditions for the image obtained through radiographing are acquired, and the reduction rate corresponding to the acquired radiographing conditions is read to reduce images by sampling the original image data, and the reduction image data are analyzed, therefore, images can be analyzed effectively.

In the medical image processing apparatus stated above, the invention is characterized in that the image analysis means conducts image analyses corresponding to the radiographing conditions acquired by the radiographing condition acquiring means.

In the medical image processing apparatus stated above, the invention is characterized in that the radiographing conditions include at least a radiographing method and a radiographing apparatus.

In the invention, the radiographing conditions include at least a radiographing method and a radiographing apparatus, and image analyses are carried out in accordance with the radiographing method and the radiographing apparatus.

BRIEF DESCRIPTION OF THE DRAWINGS

FIG. 4 is a diagram showing the structures of output characteristic data base C.

FIG. 10 is a diagram showing an example of data housing of sampling information file 15a housed in storage section 15 shown in FIG. 9.

DETAILED DESCRIPTION OF THE INVENTION

The first embodiment and the second embodiment of the invention will be explained in succession as follows, referring to the attached drawings.
(First Embodiment)

Figure 1:
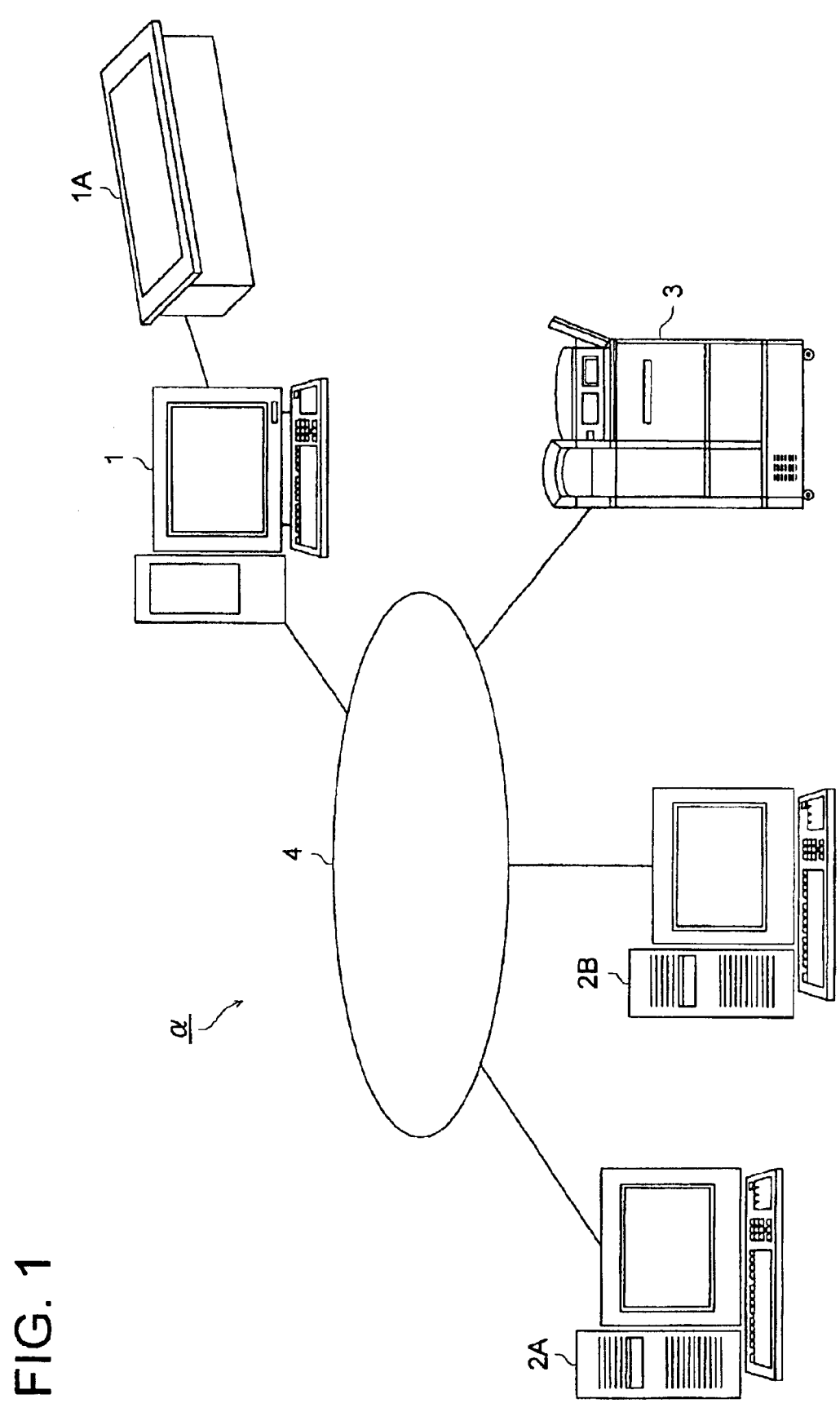
FIG. 1 is a diagram showing medical image output system a in the embodiment of the invention.

The present embodiment will be explained as follows, referring to FIG. 1–FIG. 6. First, characteristics of the embodiment as an apparatus will be explained, referring to FIG. 1–FIG. 3. FIG. 1 is a diagram showing medical image output system a in the embodiment of the invention, FIG. 2 is a diagram showing the internal structure of medical image processing apparatus 1 shown in FIG. 1, and FIG. 3 is a diagram showing the internal structures of display terminals 2A and 2B as well as imager 3 shown in FIG. 1.

As shown in FIG. 1, medical image output system a of the present embodiment is composed of medical image processing apparatus 1 that conducts control of radiographing of medical images and processing, radiographing stand 1A which radiographs medical images and transmits to the medical image processing apparatus 1, display terminals 2A and 2B each displaying and outputting medical images received from the medical image processing apparatus 1 and having different resolution, imager 3 that prints medical images received from the image processing apparatus 1 on a film for outputting, and communication network 4 that connects the medical image processing apparatus 1, display terminals 2A and 2B and imager 3.

The communication network 4 is a network such as, for example, LAN (Local Area Network), and it may include WAN (Wide Area Network), or it may be of the structure including a telephone circuit network, ISDN circuit network, a wide area communication network, exclusive lines, a movable body communication network, a communication satellite channel, CATV channel, optical communication lines, wireless communication lines and an Internet service provider who connects the foregoing.

Figure 2:
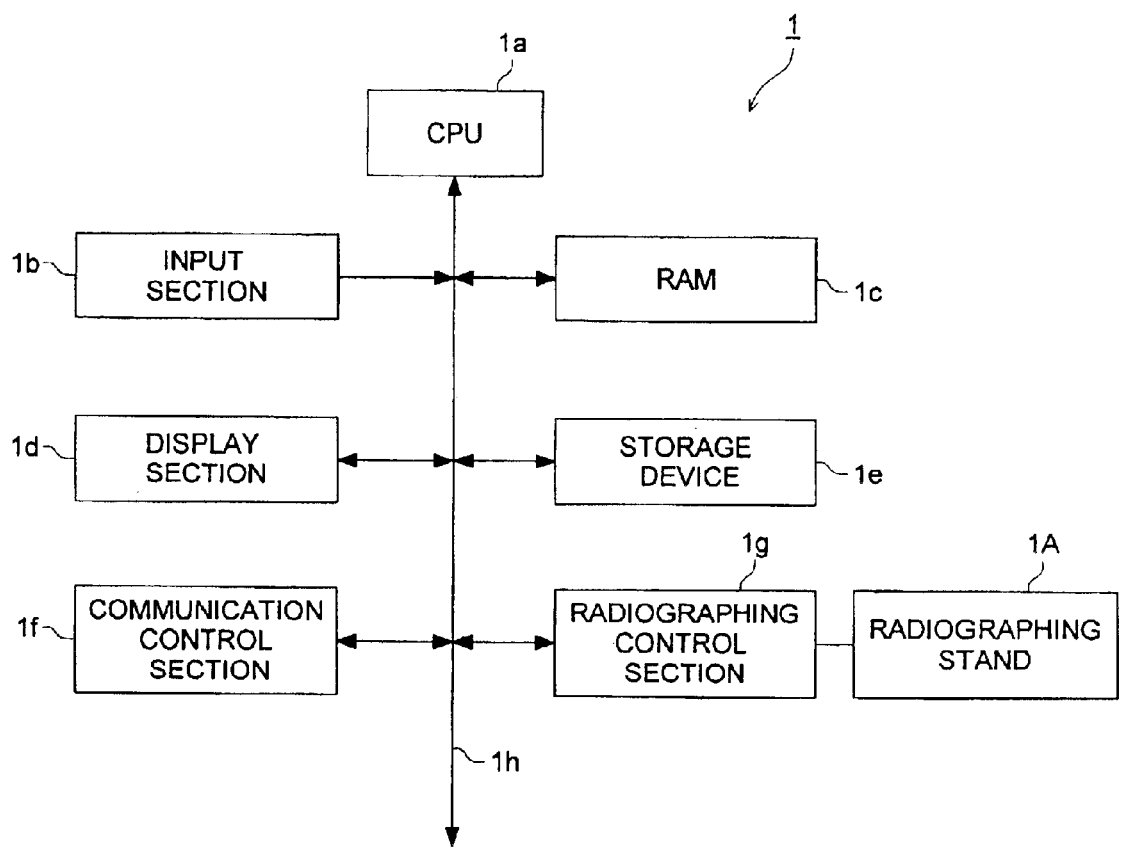
FIG. 2 is a diagram showing the internal structure of medical image processing apparatus 1 shown in FIG. 1.
Figure 3:
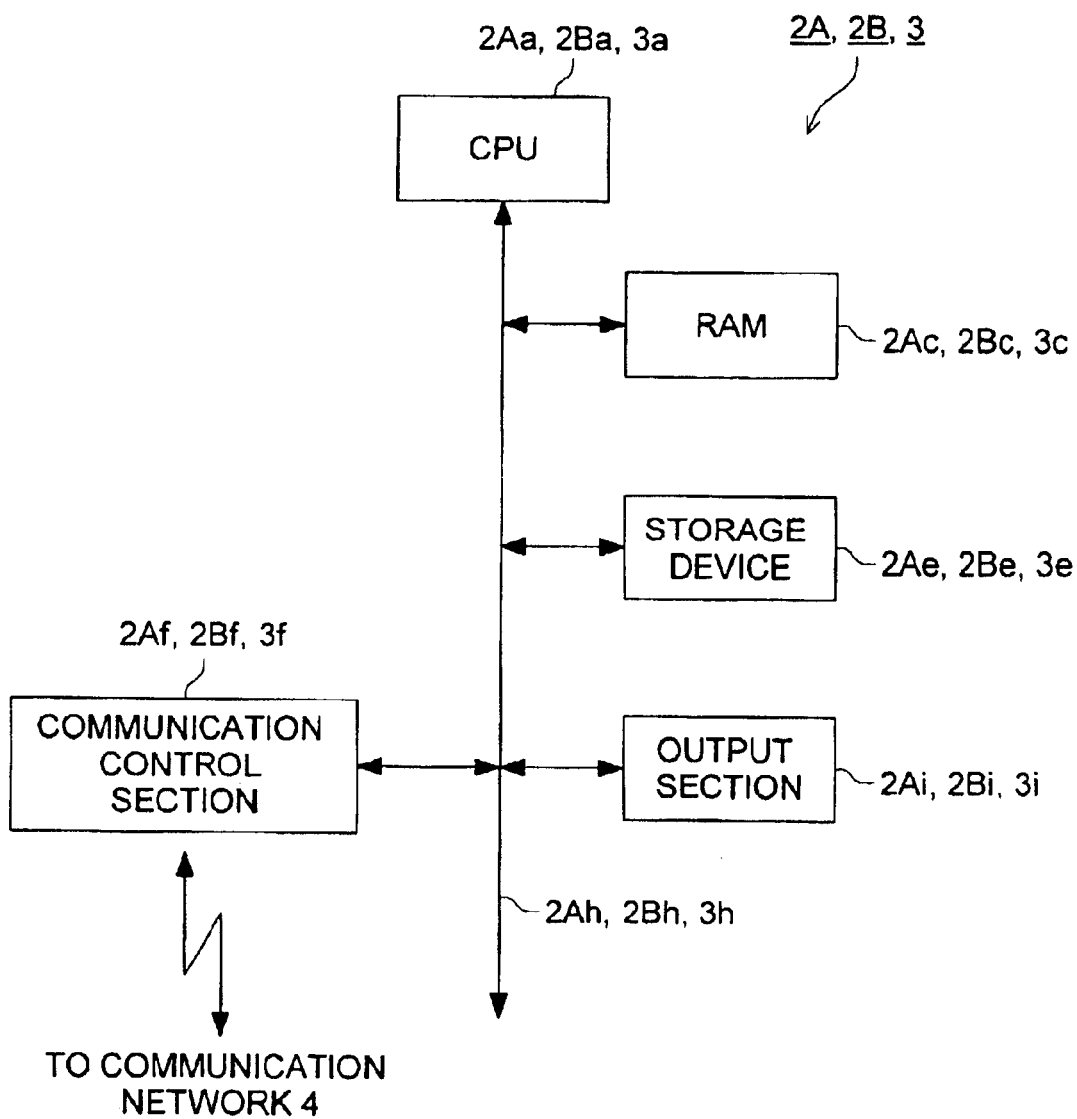
FIG. 3 is a diagram showing the internal structures of display terminals 2A and 2B as well as imager 3 shown in FIG. 1.

As shown in FIG. 2, the medical image processing apparatus 1 includes CPU (Central Processing Unit) 1a that conducts central control for each section, input section 1b through which an operator inputs information, RAM (Random Access Memory) 1c which stores information temporarily, display section 1d which indicates information to an operator, storage device 1e that stores information, communication control section if that controls sending/receiving of information to and from communication network 4, radiographing control section 1g that is connected with radiographing stand 1A to control radiographing of medical images, and bus 1h that connects CPU 1a, input section 1b, RAM 1c, display section 1d, storage device 1e, communication control section if and radiographing control section 1g.

The CPU 1a executes medical image generating and processing. Through the medical image generating and processing, the CPU 1a makes an operator to input instructions for radiographing from input section 1b, then, makes the radiographing stand 1A to radiograph medical images based on information of radiographing conditions of the inputted instruction for radiographing, and reads sampling characteristics data c1, c3 and c5 of output characteristics data base C stored in storage device 1e, and based on the sampling characteristics data c1, c3 and c5 thus read, image data obtained through radiographing aresolution converted, then, image processing characteristics data of the output characteristics data base C corresponding to output apparatus information of the inputted instruction for radiographing are read, and based on the read image processing characteristics data, the sampled image data are subjected to image processing, and thereby, the image-processed image data are transmitted to an output apparatus described in information of the output apparatus, through communication control section if and communication network 4 (see FIG. 5) CPU 1a has therein functions as a sampling means, an image processing means and a reading means described in the Structure. "Sampling" in this case means the sampling operation of analog image data, obtained through radiographing, at a predetermined interval so as to obtain a digital image data. Therefore, image data conduct certain processing on the whole image.

The input section 1b includes a key board equipped with a cursor key, a numeral inputting key and keys of various functions as well as a mouse serving as a pointing device, and outputs depressed signals depressed by an operator through a key board and positional signals of the mouse to CPU 1a.

The RAM 1c is a memory which has a memory area that houses various data such as various types of programs, input instructions, input data and results of processing so that CPU 1a can access on a random basis.

The display section 1d is composed of CRT (Cathode Ray Tube) or of LCD (Liquid Crystal Display), and it conducts display on a screen for various types of display data in accordance with display instructions inputted from CPU 1a.

The storage device 1e has a recording medium (not shown) on which programs or data are stored in advance, or which can be written on, and the recording medium is composed of a magnetic and optical recording medium, or of a recording medium which can be read by CPU 1a such as a non-volatile memory like a semiconductor. The recording medium includes one provided fixedly such as a hard disk, or a portable one which can be installed or removed freely such as CD-ROM and a memory card.

In the storage device 1e, there are housed various types of processing programs, and various types of data such as data to be processed or processed by the programs mentioned above. Both the RAM 1c and the storage device 1e are of the structure wherein internal data can be rewritten by the control of CPU 1a. The storage device 1e has therein functions of characteristics information storage means and of image storage means described in the Structures.

Further, the storage device 1e may also be of the structure wherein a part or the whole of programs and data stored in the storage device 1e are received from communication control section if through communication network 4 such as LAN and WAN, from outer equipment, and the storage device 1e may further be a storage device of the outer equipment installed in communication network 4. It is further possible to employ the structure wherein the various types of programs stated above are transmitted to or installed on the outer equipment through communication network 4.

The communication control section if is composed of a network card, modem, TA (Terminal Adapter) and a router which are for communicating with an outer equipment through communication network 4.

The radiographing stand 1A is an apparatus to apply X-rays on a patient body to radiograph it to obtain medical images, and it is an apparatus to radiograph for medical images based on information of radiographing conditions transmitted from the radiographing control section 1g of the medical image processing apparatus 1. Without being limited to this, however, the invention may also include apparatuses of a medical image radiographing method such as CT apparatus, IR apparatus, CR apparatus, a supersonic radiographing apparatus and MRI apparatus.

Incidentally, although the present embodiment is expressed by only one information processing apparatus, the medical image processing apparatus 1 may also be of the structure wherein a plurality of apparatuses are provided through communication network 4, and various types of processing are divided by respective apparatuses. In this case, load to execute each processing is divided.

As shown in FIG. 3, the display terminal 2A is equipped with CPU 2Aa, RAM 2Ac, storage device 2Ae, communication control section 2Af, bus 2Ah and output section 2Ai. The display terminal 2B is equipped with CPU 2Ba, RAM 2Bc, storage device 2Be, communication control section 2Bf, bus 2Bh and output section 2Bi. The imager 3 is equipped with CPU 3a, RAM 3c, storage device 3e, communication control section 3f, bus 3h and output section 3i.

CPU 2Aa, 2Ba and 3a, RAM 2Ac, 2Bc and 3c, storage device 2Ae, 2Be and 3e, communication control section 2Af, 2Bf and 3f, and bus 2Ah, 2Bh and 3h in each of display terminals 2A, 2B and imager 3, are the same as CPU 1a, RAM 1c, storage device 1e, communication section 1f and bus 1h in medical image processing apparatus 1, and therefore, different portions will be explained.

CPUs 2Aa, 2Ba and 3a execute medical image output processing. Through the execution of the medical image output processing, the CPUs 2Aa, 2Ba and 3a receive image-processed image data from medical image processing apparatus 1 through communication network 4 and communication control sections 2Af, 2Bf and 3f, and make output sections 2Ai, 2Bi and 3i to output the received image-processed image data (see FIG. 6).

The output section 2Ai of the display terminal 2A is an output section that displays medical images having high resolution by the use of image data of medical images, and it is composed of CRT and LCD to conduct display on a screen for various types of data in accordance with instructions for display inputted from CPU 2Aa.

Though the output section 2Bi of the display terminal 2B is the same as the output section 2Ai of the display terminal 2A, the display output section of the output section 2Bi is assumed to be one having lower resolution, compared with the output section 2Ai. Output section 3i of the imager 3 is an output section which prints visually on a film by using image data of medical images. An imager is generally required to have resolution that is higher than that of a display terminal, and output section 3i of the imager 3 is assumed to be an output section having resolution higher than that of the display terminals 2A and 2B.

Though output characteristics of the output apparatus vary depending on resolution of output and on a type of the output apparatus as in the case of display terminals 2A, 2B and imager 3, it is also possible to employ an arrangement wherein output characteristics vary in the apparatus of the same type.

Though the display terminals 2A and 2B as well as the imager 3 are installed on communication network 4 as an output apparatus, in the present embodiment, the number of the output apparatuses and types thereof are not limited to this embodiment.

Next, output characteristic data base C to be stored in storage device 1e of medical image processing apparatus 1 will be explained, referring to FIG. 4. FIG. 4 is a diagram showing the structure of output characteristic data base C.

Output characteristic data base C to be stored in storage device 1e stores image processing characteristic data c2 of various image processing, in the same way as in sampling characteristic data c1 representing output characteristics of images of display terminal 2A. The sampling characteristic data are data of a pixel size showing resolution, and for example, data with highly detailed resolution are stored in imager 3 equipped with output section 3i having high resolution. Image processing characteristic data are those of various types of image processing, and characteristic data of frequency processing are supposed to be stored in the present embodiment.

In the frequency processing, a blurred image in a certain mask size is generated, then, a practical image is subtracted from the blurred image, and specific frequency component is emphasized so that the image may be observed easily. As image processing data other than the foregoing may include data of dynamic range compression processing that corrects block of a high density portion and clearing of a low density portion, data of multi-resolution frequency processing representing the frequency processing about plural frequency components, and data of image processing of plural types.

In addition, the output characteristic data base C stores sampling characteristic data c3 representing output characteristic data of display terminal 2B, image processing characteristic data c4, sampling characteristic data c5 representing output characteristic data of imager 3, and image processing characteristic data c6.

Figure 5:
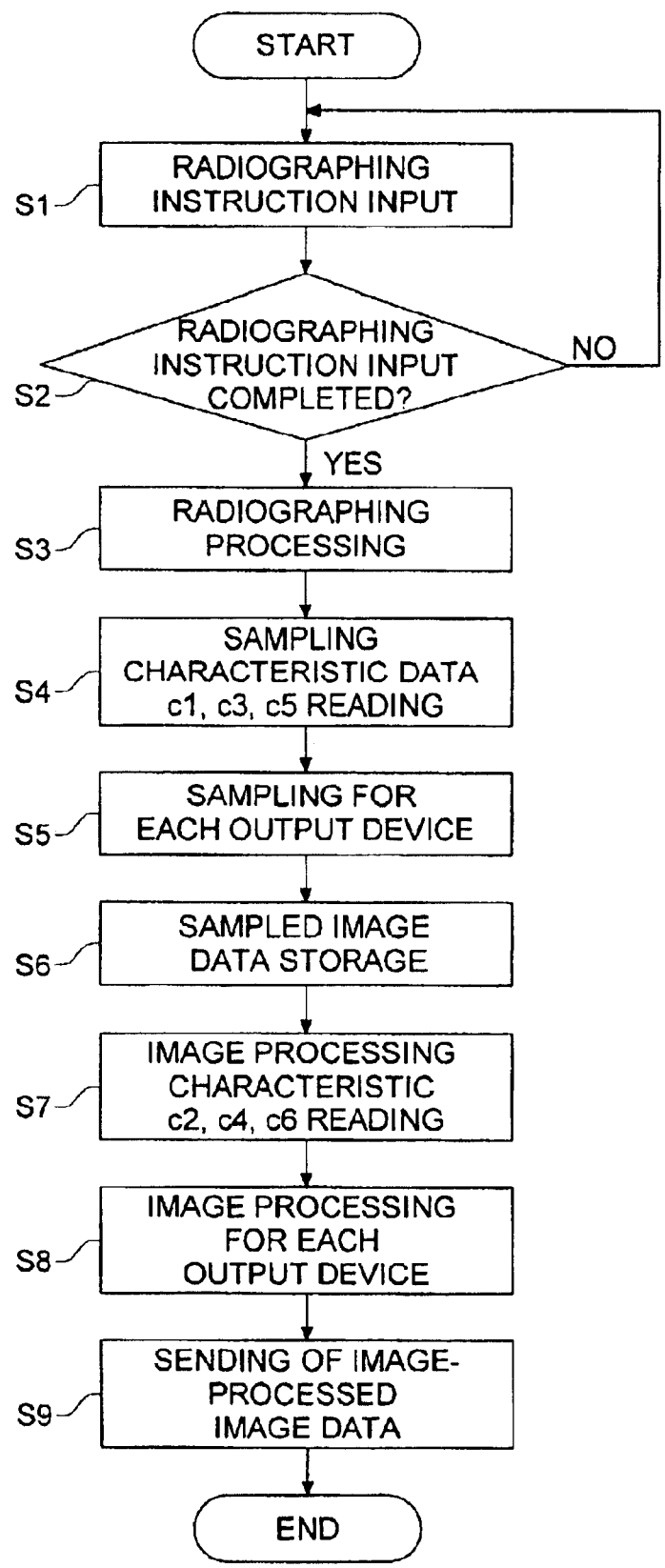
FIG. 5 is a flow chart of medical image generating and processing carried out by medical image processing apparatus 1.
Figure 6:
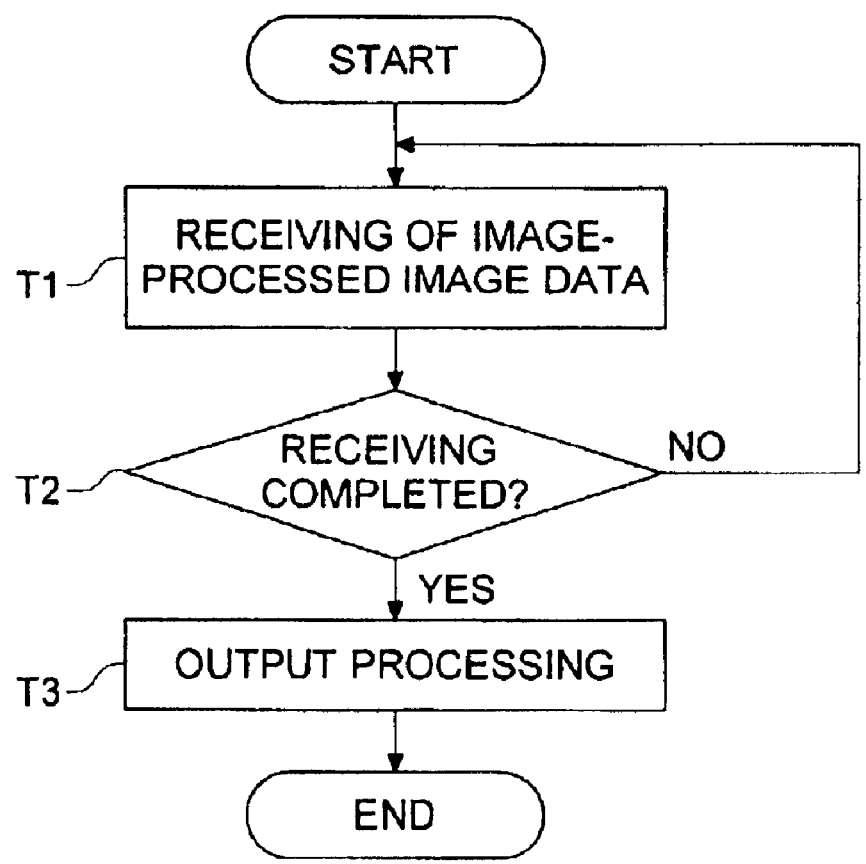
FIG. 6 is a flow chart of medical image output processing carried out by an output apparatus.

Next, operations of the present embodiment will be explained. First, medical image generating processing conducted by medical image processing apparatus 1 will be explained, referring to FIGS. 5 and 6. FIG. 5 is a flow chart of medical image generating and processing carried out by medical image processing apparatus 1 and FIG. 6 is a flow chart of medical image output processing carried out by an output apparatus. Medical image generating processing is one to transmit images radiographed by radiographing stand 1A by adapting them to output characteristics of each of display terminals 2A, 2B and imager 3 each representing an output apparatus.

Let it be assumed that output characteristic data base C established by adapting it to output characteristics of each of each of display terminals 2A, 2B and imager 3 is stored in storage device 1e in advance, in medical image processing apparatus 1. CPU 1a develops program data for medical image generating processing stored in storage device 1e in advance on RAM 1c and starts execution of medical image generating processing.

A flow chart in FIG. 5 is for illustrating the processing for realizing each function on a computer constituting medical image processing apparatus 1. This processing will be explained in an example wherein it is housed in storage device 1e in the form of the program code that can be read by CPU 1a. It is not necessary to store all functions in storage device 1e, and it may also be possible to arrange so that a part or the whole of the functions are received from communication control section 1f through communication network 4 at need to be realized. This illustration also applies equally to the medical image output processing executed by the output apparatus and to the medical image output instruction processing of the second embodiment.

First, CPU 1a makes an operator to input instructions for radiographing including information of radiographing conditions for medical images and information of the output apparatus, through input section 1b (step S1). Then, CPU 1a judges whether inputting of the instructions for radiographing has been completed or not (step S2). When the inputting of the instructions for radiographing has not been completed (step S2; NO), the flow goes back to step S1.

When the inputting of the instructions for radiographing has been completed (step S2; YES), CPU 1a transmits radiographing condition information in the instructions for radiographing inputted in step S1 to radiographing stand 1A from radiographing control section 1g, then, makes the radiographing stand 1A to radiograph medical images of a patient, and receives image data of the radiographed medical images from the radiographing control section 1g, and houses them in RAM 1c (step S3).

Then, the CPU 1a reads sampling characteristic data c1, c3 and c5 of output characteristic data base C stored in storage device 1e (step S4). Then, the CPU 1a samples the radiographed image data received in step S3, by using the sampling characteristic data c1, c3 and c5 read in step S4 (step S5).

Then, the CPU 1a stores each sampled characteristic data sampled by each of sampling characteristic data c1, c3 and c5, in the storage device 1e (step S6). Then, the CPU 1a reads image processing characteristic data corresponding to the output apparatus for output apparatus information in the instructions for radiographing inputted in step S1, among image processing characteristic data c2, c4 and c6 of output characteristic data base C stored in storage device 1e (step S7).

Then, CPU 1a conducts image processing, by the use of image processing characteristic data read in step S7, on sampled image data corresponding to the output apparatus of the output apparatus information in the instruction for radiographing inputted in the step S1, among sampled image data which weresolution converted in step S5 (step S8).

Then, the CPU 1a transmits image-processed image data which were image-processed in step S8 to the corresponding output apparatus through communication control section 1f and communication network 4 (step S9), to complete the medical image generating processing.

Since sampled image data corresponding to all output apparatuses are stored in step S6, it is possible for an operator, after execution of medical image generating processing, to input output instruction from input section 1b, and to image-process the sampled image data stored on storage device 1e corresponding to the output apparatus which has not outputted, to output to the output apparatus.

In the display terminals 2A and 2B as well as the imager 3 which represent an output apparatus, there is carried out the medical image output processing for outputting the image-processed image data transmitted in the image radiographing processing executed in medical image processing apparatus 1. In this case, display terminal 2A will be explained as a representative under the assumption that the image data are transmitted to the display terminal 2A as an output apparatus that outputs medical images. CPU 2Aa develops program data for medical image output processing stored in storage device 2Ae in advance on RAM 2Ac, and starts execution of medical image output processing.

First, the CPU 2Aa receives image-processed image data from the medical image processing apparatus 1 through communication network 4 and communication control section 2Af, and houses the received image-processed image data in RAM 2Ac (step T1). When the receiving of the image-processed image data is not completed (step T1; NO), the flow goes back to step T1.

When the receiving of the image-processed image data is completed (step T1; YES), the image-processed image data received in step T1 and stored on RAM 2Ac are outputted to be displayed from output section 2Ai on a high resolution basis (step T3), and the medical image output processing is completed. In the step T3, the image-processed image data received equally from output section 2Bi are outputted to be displayed on a low resolution basis, on the display terminal 2B. In the imager 3, the image-processed image data received equally from output section 3i are outputted on a film as a print on the basis of resolution higher than that in display terminals 2A and 2B.

Therefore, in the present embodiment, radiographed image data aresolution converted and image-processed, corresponding to each output apparatus, and it is possible to output image-processed image data by preventing image deterioration caused by resolution converting.

Further, since the sampled image data are stored in storage device 1e, even when image processing needs to be changed for execution after the medical image generating processing has been carried out, it is possible to image-process the stored and sampled image data based on the changed image processing characteristic data, if the image processing characteristic data are changed freely, and thereby to output the image-processed image data.

Figure 7:
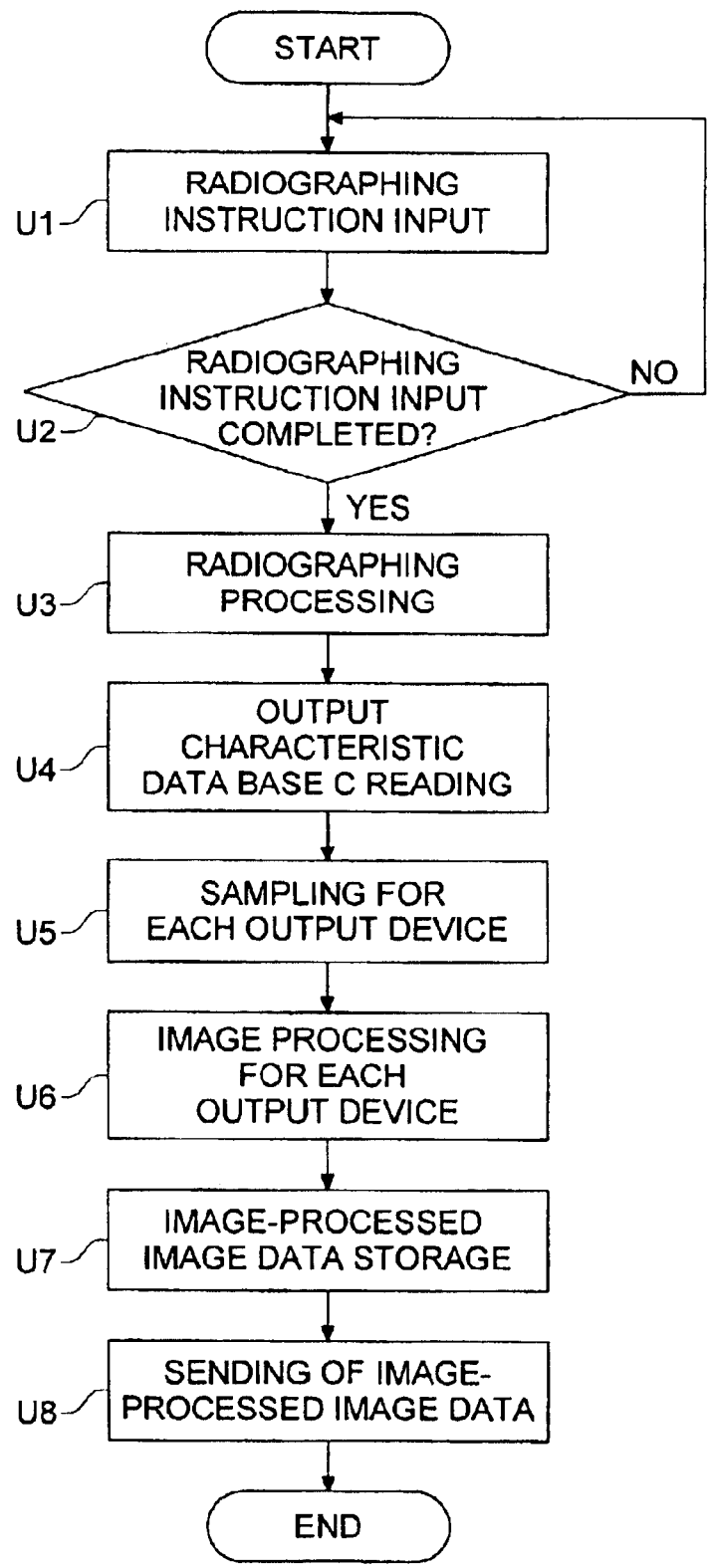
FIG. 7 is a flow chart of a variation of medical image generating and processing carried out by medical image processing apparatus 1.

Next, variations of the medical image generating processing of the present embodiment will be explained as follows, referring to FIG. 7. FIG. 7 is a flow chart of the variation of medical image generating and processing carried out by medical image processing apparatus 1. In the present variation, steps U1–U3 are the same as steps S1–S3. CPU 1a reads image processing characteristic data c2, c4 and c6, in addition to sampling characteristic data c1, c3 and c5 of output characteristic data base C (step U4).

CPU 1a samples the radiographed image data for all output apparatuses in the same way as in Step S5, by using sampling characteristic data c1, c3 and c5 of the output characteristic data base C read in step U4 (step U5). Then, the CPU 1a conducts image processing on the sampled image data sampled in step U5, by using image processing characteristic data c2, c4 and c6 of the output characteristic data base C read in step U4 (step U6).

Then, the CPU 1a stores the image-processed image data which were image-processed in step U6 in storage device 1e (step U7). Then, the CPU 1a transmits the image-processed image data corresponding to the output apparatus to the output apparatus for the output apparatus information in the instructions for radiographing in step U1 (step U8), and completes the variation of the medical image generating processing.

Therefore, when the image processing is fixed for each output apparatus, image processing characteristic data are not changed. It is therefore possible to arrange so that image-processed image data are stored in the same way as in the present variation, and the image-processed image data stored in storage device 1e can be outputted again.

(Second Embodiment)

Figure 8:
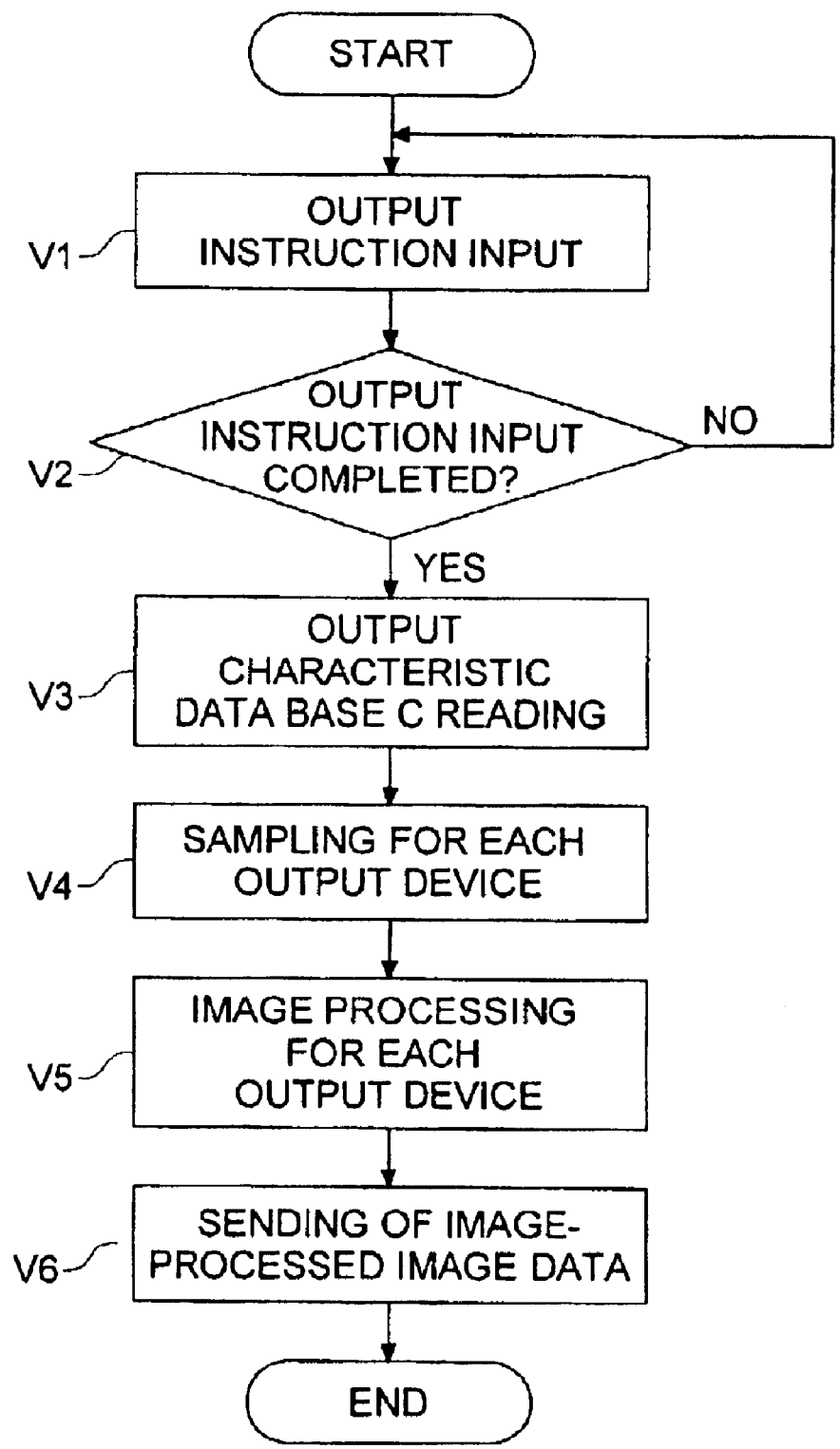
FIG. 8 is a flow chart of medical image output instruction processing carried out by medical image processing apparatus 1.

The present embodiment will be explained as follows, referring to FIG. 8. First, the characteristics as an apparatus in the present embodiment are the same as those in the First Embodiment, and different portions only will be explained.

CPU 1a executes medical image output processing. Owing to the execution of medical image output instruction processing, the CPU 1a makes an operator to input output instructions from input section 1b, then, reads sampling characteristic data of output characteristic data base C stored in storage device 1e corresponding to the output apparatus of output apparatus information in the inputted output instructions, and image information characteristic data, and based on the sampling characteristic data thus read, and it convert the resolution of the sampled image data stored in advance, and conducts image processing on the resolution converted image data based on image processing characteristic data thus read, and transmits the image-processed image data to the output apparatus described in output apparatus information through communication control section if and communication network 4 (see FIG. 8).

Next, operations in the present embodiment will be explained as follows, referring to FIG. 8. FIG. 8 is a flow chart of medical image output instruction processing carried out by medical image processing apparatus 1. Output characteristic table C is stored in storage device 1e of the medical image processing apparatus 1 in advance, and medical images are radiographed by radiographing stand 1A to be stored in storage device 1e as sampled image data after the image data of the radiographed medical images aresolution converted at a certain rate. Then, CPU 1a develops program data of medical image output instruction processing stored in storage device 1e in advance on RAM 1c to start execution of the medical image output instruction processing.

First, CPU 1a makes an operator to input output instructions including output apparatus information that outputs medical images through input section 1b (step V1). Then, the CPU 1a judges whether input of output instructions has been completed or not (step V2). When the input of output instructions is not completed (step V2; NO), the flow goes back to step V1.

When the input of output instructions is completed (step V2; YES), CPU 1a reads sampling characteristic data corresponding to the output apparatus described in the output apparatus information in output instructions of step V1 among sampling characteristic data c1, c3 and c5 of output characteristic data base C of the storage device 1e and image processing characteristic data c2, c4 and c6, and image processing characteristic data (step V3).

Then, CPU 1a samples again the sampled image data stored in storage device 1e for each output apparatus for output apparatus information, by using sampling characteristic data of output characteristic data base C read in step V3 (step V4). Then, CPU 1a conducts image processing on the resolution converted image data which were resolution converted in step V4 by using image processing characteristic data of the output characteristic data base C read in step V3, for each output apparatus of output apparatus information (step V5).

Then, CPU 1a transmits the image-processed image data which were image-processed in step V5 to an output apparatus of the output apparatus information through communication control section if and communication network 4 (step V6) to terminate medical image output processing.

In the present embodiment, therefore, it is possible to conduct resolution convertion and image processing by corresponding the sampled image data which have been sampled to the output apparatus.

Incidentally, in the first embodiment and the second embodiment, the structure may be one wherein sampled image data are stored in the data base on communication network 4, separately from medical image processing apparatus 1, and when there is given an output instruction, the stored sampled image data are acquired by the medical image processing apparatus 1 and the acquired sampled image data are subjected to image processing to be transmitted to the output apparatus, or the structure may be one wherein sampled image data are stored in the data base on communication network 4, in the variation of the first embodiment, in the same way. Concerning this, in the first embodiment, the structure may be one wherein image processing in step S8 is not carried out, and in this case, the stored sampled image data are subjected to image processing conducted by the medical image processing apparatus 1 or other apparatuses.

Further, in the second embodiment, the structure may be one wherein image processing is conducted, corresponding to the output apparatus, without resolution converting the sampled image. Further, in the second embodiment, the structure may be one wherein resolution converted image data in step V4 or image-processed image data in step V5 are stored in storage device 1e.

Though there have been explained the embodiments of the invention, the invention is not necessarily limited only to the means and methods stated above, and they may be modified freely, provided that they attain the objects of the invention and they exhibit the effects of the invention.

(Effect of the Invention)

In the invention described in Structure (1), (8), (10) or (12) in the invention, it is possible to sample the radiographed images, corresponding to the output apparatus, and to output medical images by preventing image deteriorations caused by resolution convertion.

In the invention described in Structure 2 of the invention, sampled sampled images can be subjected to image processing.

In the invention described in Structure 3 of the invention, radiographed medical images can be subjected to sampling and image processing, corresponding to the output apparatus, and medical images can be outputted by preventing resolution convertion which causes image deterioration.

In the invention described in Structure 4 of the invention, if the image processing characteristic information is changed corresponding to the output apparatus, the stored sampled images can be subjected to image processing based on the changed image processing characteristic information, because sampled images are stored in an image storage means.

In the invention described in Structure 5 of the invention, image-processed images are stored in the image storage means, and therefore, the stored image-processed images can be outputted again.

In the invention described in Structure (6), (9), (11) or (13) of the invention, sampled images of the sampled medical images can be subjected to image processing, corresponding to the output apparatus.

In the invention described in Structure (7) in the invention, sampled images of the sampled medical images can be subjected to resolution convertion and image processing, corresponding to the output apparatus.

The third embodiment of the invention will be explained in detail as follows, referring to the drawings.

Incidentally, in the present embodiment, a medical image radiographing apparatus to input images and a medical image reading apparatus will be explained as a medical image inputting apparatus, and a medical image display apparatus to output images and a film output apparatus will be explained as a medical image outputting apparatus, and when connected to the network by providing a communication control section, an image control apparatus that inputs images through the communication control section is also assumed to be included in the medical image inputting apparatus.

Further, in the present embodiment, medical image processing apparatus 10 is of the structure to be separated from the medical image inputting apparatus such as the medical image radiographing apparatus, and to be connected through I/F section 16. However, the medical image processing apparatus 10 may also be of the structure to be integrated with the medical image inputting apparatus, without being limited to the foregoing.

(Third Embodiment)

First, the structure of the third embodiment will be explained.

Figure 9:
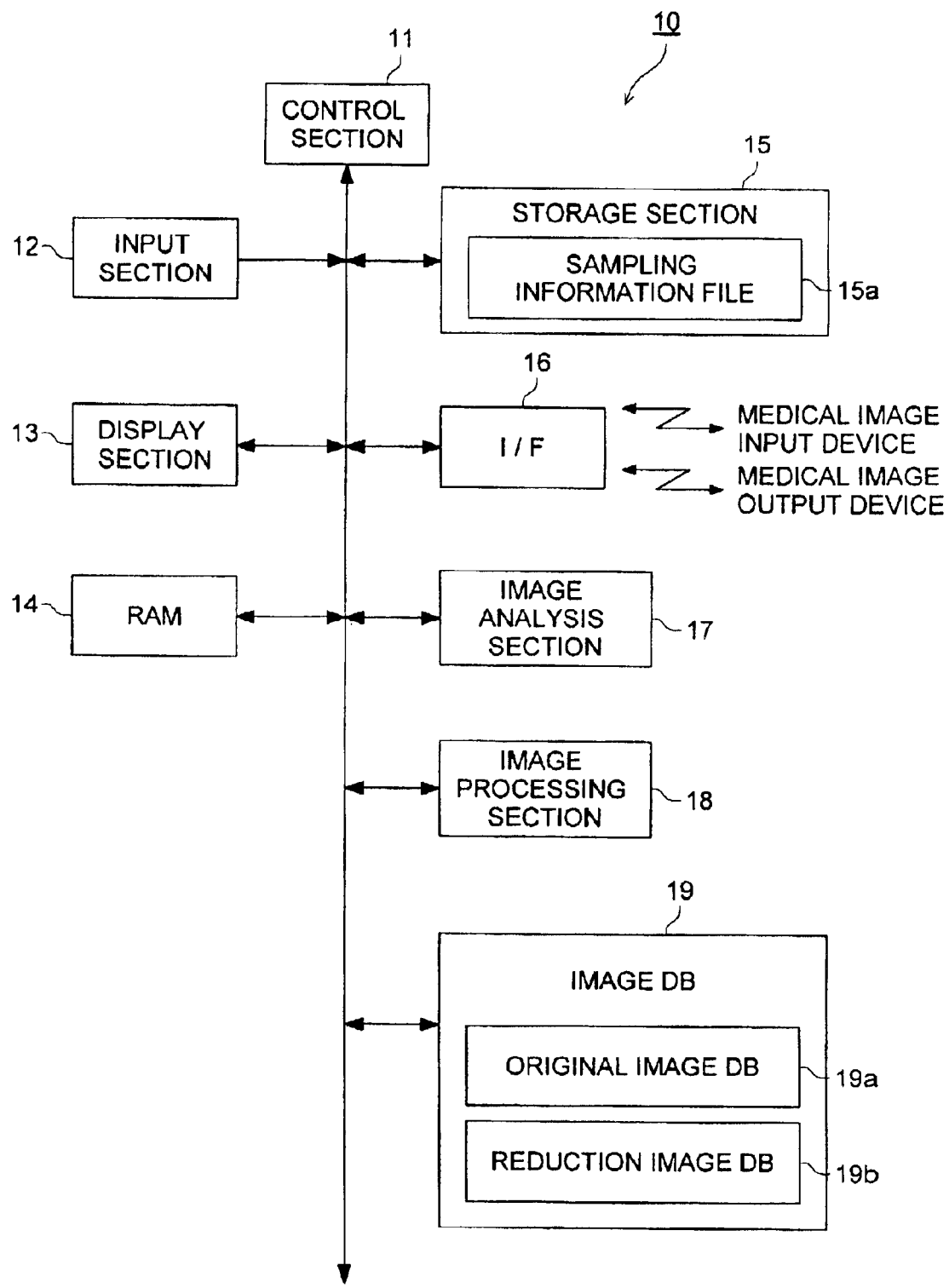
FIG. 9 is a block diagram showing the functional structure of medical image processing apparatus 10 in the embodiment to which the invention is applied.

FIG. 9 is a block diagram showing the functional structure of medical image processing apparatus 10 in the present embodiment.

As shown in FIG. 9, the medical image processing apparatus 10 is composed of control section 11, input section 12, display section 13, RAM 14, storage section 15, I/F section 16, image analysis section 17, image processing section 18 and image DB 19.

The control section 11 is composed of CPU (Central Processing Unit), and it reads various types of programs stored in the storage section 15, then, develops them on RAM 14, and controls operations of respective sections intensively in accordance with the control program. Further, the control section 11 executes various types of processing in accordance with the program developed on RAM 14, and houses the results of the processing in RAM 14 and makes the display section 13 to display them. Then, the control section 11 makes the results of the processing housed in RAM 14 to be stored at a prescribed address for storage in the storage section 15.

To be concrete, the control section 11 reads image resolution conversion program stored in the storage section 15, and executes image resolution conversion which will be described later.

In the image resolution conversion, for example: the image reduction processing, the control section 11 houses digital image data which are inputted from the I/F section 16 in original image DB 19a as original image data, and acquires radiographing information including a radiographing method and a radiographing apparatus. Then, the control section 11 acquires sampling information corresponding to radiographing information acquired by reading sampling information file 15a, then, reads a reduction rate established in the sampling information, and makes the original image data to be analyzed in terms of image housed in original image DB 19a to conduct reduction processing (digital to digital sampling) on image processing section 18 at the reduction rate obtained by reading, to generate digital reduction image data and thereby to house them in reduction image DB 19b. Namely, the control section 11 has a function as a means to acquire radiographing conditions.

The input section 12 includes a key board equipped with a cursor key, a numeral inputting key and keys for various types of functions, and outputs to the control section 11 depressed signals corresponding to the keys depressed by the key board. Incidentally, the input section 12 may also be equipped with a pointing device such as a mouse or a touch panel, or other input devices.

The display section 13 is composed of LCD (Liquid Crystal Display) and CRT (Cathode Ray Tube), and it displays input instructions from the input section 12 on the display screen, in accordance with instructions of a display signal inputted from the control section 11. Further, the display section 13 may also be arranged to display, on the display screen, the image processed by image processing section 18 in terms of image.

In each type of processing executed and controlled by the control section 11, RAM (Random Access Memory) 14 forms temporary housing areas for a system program which is read from the storage section 15 and can be executed on the medical image processing apparatus 10, a control program, input or output data and a parameter.

The storage section 15 has a recording medium (not shown) on which a program or data are stored in advance, and this recording medium is composed of a magnetic or optical recording medium or of a semiconductor memory. This recording medium is provided on the storage section 15 fixedly, or it is mounted detachably, and a system program corresponding to the medical image processing apparatus 10, each type of processing program corresponding to the aforesaid system program and data processed by each processing program are stored in the recording medium. These respective processing programs are housed in the form of a program code which can be read, and the control section 11 executes operations in accordance with the program code in succession.

The storage section 15 houses therein sampling information file 15a shown in FIG. 10, in a file form wherein updating is possible. To be detailed, the sampling information file 15a stores therein radiographing methods employed (for example, adult breast front, infant abdomen front), radiographing apparatuses for images (for example, a simple radiographing apparatus, a contrast radiographing apparatus, a scanner, an enlargement radiographing apparatus), a reduction rate to be applied when generating reduction image data by sampling from original image data for image analyses (for example, information showing a size of a pixel after reduction is shown in a way of 2.8 mm pitch or 1.4 mm pitch), and image analyses information showing image analysis parameter applied in the aforesaid case (for example, analysis parameter 1), so that each of the foregoing may correspond each other. For example, as shown in FIG. 10, sampling information A shows that when a radiographing method and a radiographing apparatus are represented respectively by "adult, breast, front" and "simple radiographing apparatus", sampling is conducted at the reduction rate of "2.8 mm pitch" and an image analysis is conducted by the parameter of "analysis parameter 1" when the generated reduction image data are analyzed. Namely, the storage section 15 has a function as a sampling condition storage means.

Incidentally, with respect to the reduction rate, a reduction rate which realizes optimum image analyses for the radiographing method and radiographing apparatus is assumed to be obtained in advance by taking the statistics. The reduction rate which makes the optimum image analysis possible is a reduction rate which can make the processing time shortest without lowering processing accuracy for image analysis.

The I/F section 16 is composed of an input interface for connecting with a medical image input apparatus such as a medical image radiographing apparatus, and of an output interface for connecting with a medical image output apparatus such as a medical image display apparatus a film output apparatus, and it outputs digital image data inputted from a medical image inputting apparatus to image DB 19. Further, when instructions for output are given by the control section 11, image data thus inputted are outputted to a medical image outputting apparatus.

The image analysis section 17 is provided with a plurality of image analysis parameters in accordance with radiographing methods and radiographing apparatuses, and conducts image analyses with analysis parameters instructed for the inputted reduction image data, for coping with image analyses instructions given by the control section 11. In a detailed expression, the image analysis section 17 recognizes an image area to be subjected to image processing in a method appropriate for the radiographing method and the radiographing apparatus, to prepare an accumulated histogram in the aforesaid image area, and based on the results of the prepared accumulated histogram, the image analysis section 17 recognizes an area important for diagnosis (a region of interest) with an analysis parameter appropriate for the radiographing method and the radiographing apparatus, to determine its image processing condition (for example, gradation processing condition) and thereby to output to the control section 11 as a result of analyses. Namely, the image analysis section 17 has a function as an image analysis means.

The image analysis stated above will be explained concretely as follows. In the case of medical images, various regions such as a breast, a head and extremities are radiographed in various postures such as a side and a front, and its radiographing method includes many ways such as a simple radiographing requiring no specific technology, tomograpyy for radiographing a tomogram and contrast radiographing employing a contrast medium such as barium. When analyzing images, therefore, it is preferable to prepare analysis parameters suitable for the radiographing method and the radiographing apparatus. For example, if a fixed area which is lengthwise and square mostly corresponding to a lengthwise subject is recognized as an image area to be analyzed in terms of image, in the case of analyses for an image of a breast of an adult taken from the front through simple radiographing, and if a fixed area which is oblong and square mostly corresponding to a subject which is oblong and is in an ellipse form mostly is recognized as an image area to be analyzed in terms of image, in the case of an abdomen which has been subjected to tomography, an unwanted area is not included in diagnoses and analysis processing efficiency is excellent.

The image processing section 18 conducts various types of image data processing such as frequency processing for adjusting sharpness of an image on the inputted image data in accordance with instructions from the control section 11, gradation processing for adjusting contrast, or various types of image data processing such as dynamic range compression processing for putting an image with a broad dynamic range in an easy-to-see density range without lowering contrast in a detailed part of a subject. Further, the image processing section 18 reduces (samples) the inputted original image data at the instructed reduction rate when sampling for image analyses is instructed by the control section 11, and outputs the reduction image data to image DB 19. Namely, the image processing section 18 has a function as a sampled image data generating means.

The image DB (Data Base) 19 is composed of original image DB 19a for housing digital image data inputted from I/F section 16 as original image data and of reduction image DB for housing reduction digital image data generated for image analyses. Further, the image DB 19 outputs the image data designated from image data to be housed to display section 13 and image processing section 18, in accordance with instructions from the control section a region of interest11 for outputting image data. Namely, the image DB 19 has a function as an original image data storage means.

Next, operations in the third embodiment will be explained.

First, image reduction processing for conducting digital to digital sampling from original image data for analyzing image data inputted through I/F section 16, and thereby for generating reduction image data will be explained, referring to FIG. 10.

FIG. 10 is a flow chart for illustrating image reduction processing executed by the control section 11 in FIG. 9.

Figure 11:
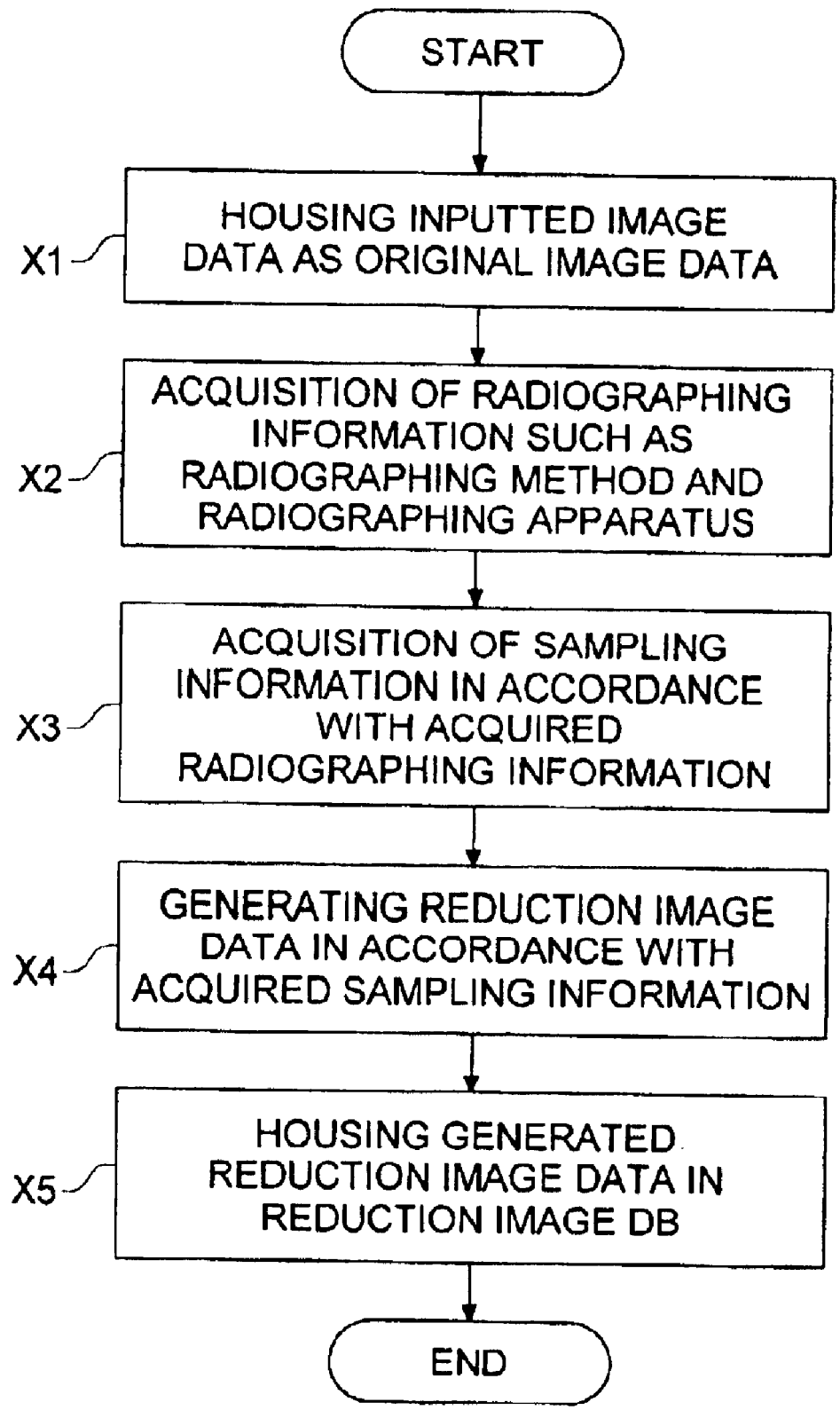
FIG. 11 is a flow chart illustrating image reduction processing carried out by control section 11 shown in FIG. 9.

In FIG. 10, the control section 11 houses image data inputted from the medical image radiographing apparatus in original image DB 19a through I/F section 16, as original image data (Step X1 in FIG. 11). Then, radiographing information concerning the image data is acquired from the medical image radiographing apparatus through the I/F section 16 (Step X2). In the radiographing information, there are included radiographing method information and radiographing apparatus information, and with respect to acquisition of the radiographing information, it is possible either to acquire radiographing information by making radiographing information inputted by a user on the medical image radiographing apparatus side in the course of radiographing to be added to the image data as supplementary information and thereby by reading the supplementary information, or to acquire radiographing information by displaying an input image into which radiographing information is inputted on display section 13 and by making a user to input from input section 12.

Next, the control section 11 reads sampling information file 15a for retrieval, and acquires sampling information corresponding to the acquired radiographing information (Step X3). Now, acquisition of sampling information will be explained concretely as follows, referring to FIG. 10. For example, when the image to be analyzed is an image of an adult breast front that is radiographed simply by a radiographing apparatus, sampling information wherein a radiographing method is represented by "adult breast front" and a radiographing apparatus is represented by "simple radiographing apparatus" is retrieved. In this case, the sampling information corresponding to the retrieval condition is "sampling information A", and the sampling information A is acquired as information used in the course of sampling.

Then, the control section 11 reads the reduction rate to be applied in the case of sampling from the acquired sampling information, then, acquires original image data to be subjected to image analysis from original image DB 19a, and makes image processing section 18 to conduct reduction processing (sampling) at the reduction rate, to generate reduction image data (Step X4 in FIG. 11). Then, the generated reduction image data are housed in reduction image DB 19b (Step X5 in FIG. 11) to terminate the image reduction processing.

After the image reduction processing mentioned above, the control section 11 reads image analysis information from the sampling information applied in the case of the generation of the reduction image data and determines an image analysis parameter to be applied, to make image analysis section 17 to conduct image analyses. This will be explained in detail, referring to FIG. 10. When sampling information applied in the case of generation of reduction image data is "sampling information A", for example, "analysis parameter 1" is used for conducting image analyses, because image analysis information of the sampling information A is "analysis parameter 1".

As stated above, a reduction rate and an image analysis parameter which can conduct image analyses corresponding to the method of radiographing images and radiographing conditions of a radiographing apparatus, are stored in advance as sampling information to be corresponded each other. Therefore, when generating reduction image data from original image data through sampling, it is possible to analyze images efficiently and to improve processing accuracy for the image analysis, by conducting retrieval and reading of sampling information corresponding to its radiographing method for images and radiographing conditions for the radiographing apparatus.

Incidentally, the description of the aforementioned third embodiment is an example of preferable medical image processing apparatus 10 relating to the invention, and the invention is not limited to this.

For example, in the explanation, a reduction rate corresponding to the radiographing method and a reduction rate corresponding to the radiographing apparatus are established in advance. However, the reduction rate may also be for only the radiographing method or only the radiographing apparatus.

Further, the reduction rate used in the case of sampling is expressed by a size of one pixel after the reduction as in "2.8 mm pitch", in the aforementioned explanation. However, it is also possible to express with a magnification such as "one third" or the like, provided that the expression shows a condition for the reduction.

Besides, detailed structures and detailed operations of medical image processing apparatus 10 in the third embodiment may also be modified properly without departing from the spirit and objects of the invention.

In the third embodiment, the reduction rate that makes the processing time to be shortest is stored in advance in accordance with radiographing conditions for images without lowering the processing accuracy for image analyses, then, the radiographing condition for the image radiographed is acquired, the reduction rate corresponding to the radiographing conditions thus acquired is read and reduced by sampling the original image data, and thereby, the reduced image data are analyzed, thus, images are analyzed efficiently.

Further, radiographing conditions include at least a radiographing method and a radiographing apparatus, and image analyses are conducted depending on the radiographing method and the radiographing apparatus. It is therefore possible to conduct flexible image analyses and to enhance processing accuracy for image analyses.

What is claimed is:

1. A medical image processing apparatus for reading a medical image obtained through radiographing and for outputting said medical image to a plurality of output devices, comprising:

a characteristics information storage means for storing characteristics information, including sampling characteristics information showing resolution of each one of said output devices;

a reading means for reading said medical image obtained through radiographing; and a sampling means for conducting sampling of said medical image read by said reading means, in use of sampling characteristics information among characteristics information stored in said characteristics information storage means, for each one of said output devices so that a sampled image is generated.

2. The medical image processing apparatus of claim 1, further comprising an image processing means for processing said sampled image generated by said sampling means so that a processed image is obtained.

3. The medical image processing apparatus of claim 2, wherein said characteristics information includes image processing characteristics information, showing image processing characteristics of each one of said output devices, and said image processing means processes sampled image generated by said sampling means in use of image processing characteristics information among characteristics information stored in said characteristics information storage means.

4. The medical image processing apparatus of claim 1, further comprising an image storage means for storing said sampled image generated by said sampling means.

5. The medical image processing apparatus of claim 2, further comprising an image storage means for storing said processed image processed by said image processing means.

6. A medical image processing apparatus for reading sampled medical image and for outputting said medical image to a plurality of output devices, comprising:

a characteristics information storage means for storing characteristics information, including image processing characteristics information showing image processing characteristics of each one of said output devices;

a reading means for reading said sampled medical image; and an image processing means for processing, for each one of said output devices, said sampled medical image read by said reading means in use of image processing characteristics information among characteristics information stored in said characteristics information storage means.

7. The medical image processing apparatus of claim 6, wherein said characteristics information includes sampling characteristics information showing resolution of each one of said output devices;

said medical image processing apparatus further comprises a resolution conversion means for converting said sampled image read by said reading means again for each one of said output devices, in use of sampling characteristics information among characteristics information stored in said characteristics information storage means, so that a resolution converted image is obtained; and said image processing means processes, for each one of said output devices, said resolution converted image in use of image processing characteristics information among characteristics information stored in said characteristics information storage means.

8. An medical image processing method for reading medical image obtained through radiographing and for outputting said medical image to a plurality of output devices, comprising the steps of:

reading said medical image obtained through radiographing;

reading sampling characteristics information as characteristics information from said characteristics information storage means that stores characteristics information including sampling characteristics information showing resolution of each one of said output devices; and sampling said medical image for each one of said output devices in use of said sampling characteristics information read.

9. An medical image processing method for reading sampled medical image and for outputting said medical image to a plurality of output devices, comprising the steps of:

reading said sampled medical image;

reading image processing characteristics information as characteristics information from said characteristics information storage means that stores characteristics information including image processing characteristics information showing image processing characteristics of each one of said output devices; and processing said sampled medical image for each one of said output devices in use of said image processing characteristics information.

10. A program for a computer, comprising the steps of:

reading medical image obtained through radiographing;

reading sampling characteristics information as characteristics information from said characteristics information storage means that stores characteristics information including sampling characteristics information showing resolution of a plurality of output devices; and sampling said medical image for each one of said output devices in use of said sampling characteristics information.

11. A program for a computer, comprising the steps of:

reading out sampled medical image;

reading image processing characteristics information as characteristics information from said characteristics information storage means that stores characteristics information including image processing characteristics information showing image processing characteristics of a plurality of output devices; and processing said sampled medical image, read out for each one of said output devices, in use of said image processing characteristics information read.

12. A recording medium capable of being read by a computer and having a program for executing the steps of:

reading medical image obtained through radiographing;

reading sampling characteristics information as characteristics information from said characteristics information storage means that stores characteristics information including sampling characteristics information showing resolution of a plurality of output devices; and sampling said medical image for each one of said output devices in use of said sampling characteristics information.

13. A recording medium capable of being read by a computer and having a program for executing the steps of:

reading out sampled medical image;

reading image processing characteristics information as characteristics information from said characteristics information storage means that stores characteristics information including image processing characteristics information showing image processing characteristics of a plurality of output devices; and processing said sampled medical image, read out for each one of said output devices, in use of said image processing characteristics information read.

14. A medical image processing apparatus for conducting image processing on image inputted by a medical image inputting apparatus, comprising:

an original image data storage means for storing said image, inputted by said medical image inputting apparatus, as original image data;

a sampling condition storage means for storing a sampling condition in correspondence with a radiographing condition of said image for every radiographing condition when said original image data is resolution converted so as to generate resolution converted image data;

a radiographing condition acquiring means for acquiring said radiographing condition for said image, inputted from said medical image input apparatus;

a sampled image data generating means for reading out a sampling condition corresponding to said radiographing condition, acquired from said sampling condition storage means, so as to sample said original image data according to said sampling condition to generate sampled image data; and an image analysis means for conducting image analysis on said sampled image data.

15. The medical image processing apparatus of claim 14, wherein said sampled image data generating means samples said original image data and generates reduction image data; said sampling condition is a reduction rate which is used when said sampled image data generating means generates said reduction image data; and said reduction rate is to make said processing time shortest without lowering said processing accuracy for said image analysis by said image analysis means.

16. The medical image processing apparatus of claim 14, wherein said image analysis means conducts said image analysis in accordance with said radiographing condition, acquired by said radiographing condition acquiring means.

17. The medical image processing apparatus of claim 14, wherein said radiographing condition includes at least information to identify a radiographing method and a radiographing apparatus.

18. A medical image processing method for conducting image processing on image inputted by a medical image inputting apparatus, comprising the steps of:

storing said image, inputted by said medical image inputting apparatus, to an original image data storage means as original image data;

storing a sampling condition to a sampling condition storage means in correspondence with a radiographing condition of said image for every radiographing condition when said original image data is sampled so as to generate sampled image data;

acquiring said radiographing condition for said image, inputted from said medical image input apparatus;

reading out a sampling condition, corresponding to said radiographing condition, from said sampling condition storage means, so as to sample said original image data according to said sampling condition to generate sampled image data; and conducting image analysis on said sampled image data.

19. A program executed by a computer for controlling a medical image processing apparatus so as to conduct image processing on an image inputted by a medical image input apparatus, comprising the steps of:

storing said image, inputted by said medical image inputting apparatus, to an original image data storage means as original image data;

storing a sampling condition to a sampling condition storage means in correspondence with a radiographing condition of said image for every radiographing condition when said original image data is sampled so as to generate sampled image data;

acquiring said radiographing condition for said image, inputted from said medical image input apparatus;

reading out a sampling condition, corresponding to said radiographing condition, from said sampling condition storage means, so as to sample said original image data according to said sampling condition to generate sampled image data; and conducting image analysis on said sampled image data.

20. A recording medium having a program to be executed by a computer for controlling a medical image processing apparatus so as to conduct image processing on an image inputted by a medical image input apparatus, comprising the program code steps of:

storing said image, inputted by said medical image inputting apparatus, to an original image data storage means as original image data;

storing a sampling condition to a sampling condition storage means in correspondence with a radiographing condition of said image for every radiographing condition when said original image data is sampled so as to generate sampled image data;

acquiring said radiographing condition for said image, inputted from said medical image input apparatus;

reading out a sampling condition, corresponding to said radiographing condition, from said sampling condition storage means, so as to sample said original image data according to said sampling condition to generate sampled image data; and conducting image analysis on said sampled image data.

* * * * *